United States Patent [19]

Botta et al.

[11] 4,278,791

[45] Jul. 14, 1981

[54] BENZIMIDAZOLYL-2-ALKANE-PHOS-PHONIC ACIDS

[75] Inventors: Artur Botta; Heinz-Joachim Rother; Günther Teichmann, all of Krefeld-Uerdingen, Fed. Rep. of Germany

[73] Assignee: Bayer Aktiengesellschaft, Leverkusen, Fed. Rep. of Germany

[21] Appl. No.: 101,977

[22] Filed: Dec. 10, 1979

[30] Foreign Application Priority Data

Dec. 22, 1978 [DE] Fed. Rep. of Germany ....... 2855659

[51] Int. Cl.³ .......................... C09B 23/14; C07F 9/28
[52] U.S. Cl. .................................. 542/412; 548/113; 106/308 N; 106/300; 106/304; 422/7; 422/15
[58] Field of Search ................. 548/112, 113; 542/412

[56] References Cited

U.S. PATENT DOCUMENTS

| | | | |
|---|---|---|---|
| 3,632,755 | 1/1972 | Goring et al. | 542/412 |
| 3,818,030 | 6/1974 | Timmler et al. | 548/112 |
| 4,000,079 | 12/1976 | Rasp et al. | 548/330 |

*Primary Examiner*—Henry R. Jiles
*Assistant Examiner*—Jane T. Fan
*Attorney, Agent, or Firm*—Sprung, Felfe, Horn, Lynch & Kramer

[57] ABSTRACT

A benzimidazolyl-2-alkane-phosphonic acid of the formula

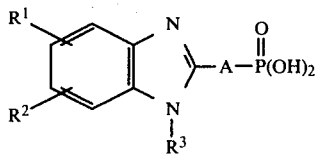

wherein
 $R^1$ and $R^2$ are identical or different and denote hydrogen, lower alkyl, phenyl, halogen, trifluoromethyl, nitro or lower alkoxy, or together form a fused-on benzene ring,
 $R^3$ denotes hydrogen, lower alkyl or phenyl or benzyl which is optionally substituted by lower alkyl or halogen and
 A denotes a straight-chain or branched, saturated or unsaturated bivalent hydrocarbon radical with 1 to 15 carbon atoms, which can be substituted by phenyl which is optionally substituted by lower alkyl or halogen or by carboxyl or the phosphonic acid group, and its salt with an inorganic or organic base or acid, and a method of preparing the same by contacting an o-arylene diamine of the formula

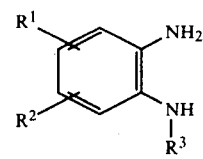

wherein
 $R^1$, $R^2$ and $R^3$ have the meaning given above, with a phosphonocarboxylic acid of the formula

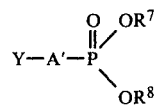

wherein
 Y denotes carboxyl, carbalkoxy, carbophenoxy, cyano, carbamido or carbochloride,
 $R^7$ and $R^8$ are identical or different and denote hydrogen, lower alkyl or phenyl, or together can form a ring, by means of an ethylene or propylene bridge, and
 A' denotes a straight-chain or branched, saturated or unsaturated bivalent hydrocarbon radical with 1 to 15 carbon atoms, which can be substituted by phenyl which is optionally substituted by lower alkyl or halogen or by Y or the group

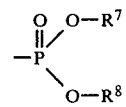

wherein
 Y, $R^7$ and $R^8$ have the abovementioned meaning, in the presence of an acid..

The new benzimidazolyl-2-alkane-phosphonic acids are useful as anti-corrosion agents (corrosion inhibitors), as well as wetting agents for aqueous suspensions of pigments and fillers.

6 Claims, No Drawings

BENZIMIDAZOLYL-2-ALKANE-PHOSPHONIC ACIDS

The invention relates to new benzimidazolyl-2-alkane-phosphonic acids and their corresponding salts, a process for their preparation and their use as anti-corrosion agents or wetting agents.

New benzimidazolyl-2-alkane-phosphonic acids of the formula

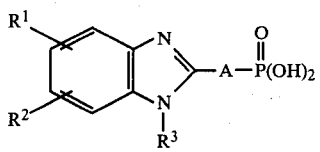

wherein
$R^1$ and $R^2$ are identical or different and denote hydrogen, lower alkyl, phenyl, halogen, trifluoromethyl, nitro or lower alkoxy, or together form a fused-on benzene ring,
$R^3$ denotes hydrogen, lower alkyl or phenyl or benzyl which is optionally substituted by lower alkyl or halogen and
A denotes a straight-chain or branched, saturated or unsaturated bivalent hydrocarbon radical with 1 to 15 carbon atoms, which can be substituted by phenyl which is optionally substituted by lower alkyl or halogen or by carboxyl or the phosphonic acid group,
and their salts with inorganic or organic bases and acids have been found.

Lower alkyl radicals for the process according to the invention can be straight-chain or branched hydrocarbon radicals with preferably 1 to 6 carbon atoms. Examples which may be mentioned are: Methyl, ethyl propyl, isopropyl, butyl, isobutyl, tert.-butyl, pentyl, isopentyl, hexyl and isohexyl.

Halogen radicals for the process according to the invention can be fluorine, chlorine, bromine or iodine, preferably fluorine and chlorine.

Lower alkoxy radicals for the process according to the invention can contain a straight-chain or branched hydrocarbon radical with preferably 1 to 6 carbon atoms, in particular 1 to 2 carbon atoms. Examples which may be mentioned are: methoxy, ethoxy propoxy, isopropoxy, butoxy, isobutoxy, pentoxy, isopentoxy, hexoxy and isohexoxy.

If $R^1$ and $R^2$ together form a benzene ring which is fused onto the aromatic nucleus of the benzimidazolyl radical, a naphthimidazolyl radical is produced.

A can be a straight-chain or branched, saturated or unsaturated, bivalent hydrocarbon radical with 1 to 15, preferably with 1 to 12, and in particular with 1 to 6, carbon atoms. Examples which may be mentioned are: methylene, ethylene, vinylene, propylene, butylene, butenylene, pentylene, hexylene, hexenylene, cyclohexylene, cyclopentylene, heptylene, octylene, decylene and dodecylene.

These radicals can optionally be substituted by phenyl, tolyl, ethylphenyl, xylyl, chlorophenyl, carboxyl and/or phosphono.

The salts of the benzimidazolyl-2-alkane-phosphonic acids are likewise new. Examples of these salts which may be mentioned are the compounds which are formed by reacting the benzimidazolyl-2-alkane-phosphonic acids according to the invention with basic compounds or with acids. Examples of basic compounds which may be mentioned are the alkali metal hydroxides or oxides and alkaline earth metal hydroxides or oxides, ammonia and amines. As dibasic acids, the benzimidazolyl-2-alkane-phosphonic acids according to the invention can, of course, form salts both with one equivalent and with two equivalents of a basic compound.

Examples of preferred salts are the sodium, potassium, magnesium, calcium, zinc, chromium and molybdenum, ammonium, lower alkyl-ammonium, di-lower alkyl-ammonium and tri-lower alkyl-ammonium salts.

Examples of acids which may be mentioned are mineral acids, such as hydrochloric acid, sulphuric acid, nitric acid and phosphoric acid, and strong organic acids, such as trifluoroacetic acid, methanesulphonic acid, benzenesulphonic acid and toluenesulphonic acid.

Examples of preferred salts are the sulphates, phosphates and sulphonates.

The new benzimidazolyl-2-alkane-phosphonic acids according to the invention can, of course, also exist in their possible tautomeric forms. Thus, for example, as zwitter-ion compounds they can also correspond to the general formula

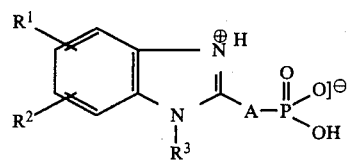

For reasons of simplicity, however, hereinafter they are characterised by the general formula I.

Compounds of the formula

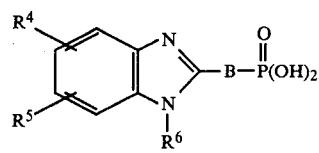

wherein
$R^4$ and $R^5$ are identical or different and denote hydrogen, methyl, chlorine, methoxy or nitro,
$R^6$ denotes hydrogen, methyl, benzyl or phenyl and
B denotes methylene, ethylene, propylene, butylene, vinylene, phenylvinylene, carboxyethylene, carboxypropylene, dicarboxypropylene, dicarboxybutylene, phosphonopropylene, phosphonobutylene or carboxydiphosphonobutylene, may be mentioned as preferred new benzimidazolyl-2-alkane-phosphonic acids.

The following benzimidazolyl-2-alkane-phosphonic acids may be mentioned as specific examples: benzimidazolyl-methanephosphonic acid, -ethanephosphonic acid, -vinylphosphonic acid, -propanephosphonic acid, -carboxyethanephosphonic acid, -β-styrylphosphonic acid, -1-carboxy-1-carboxy-methyl-propanephosphonic acid and -3-carboxy-butane-1,3-diphosphonic acid and 1-methylbenzimidazolyl-ethanephosphonic acid; 1-phenylbenzimidazolyl-, 1-benzylbenzimidazolyl-, 5-methylbenzimidazolyl-, 5-chlorobenzimidazolyl-, 4,6-dimethylbenzimidazolyl- and 4- or 5-methylbenzimidazolyl-methanephosphonic acid; 5-nitrobenzimidazolyl-, 5-methoxybenzimidazolyl- and 4- or 5-methyl-benzimidazolyl-ethanephosphonic acid.

Furthermore, a process has been found for the preparation of the new benzimidazolyl-2-alkane-phosphonic acids, which is characterized in that o-arylenediamines of the formula

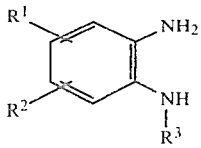

wherein $R^1$, $R^2$ and $R^3$ have the abovementioned meaning, are reacted with phosphonocarboxylic acid compounds of the formula

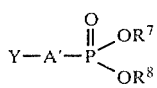

wherein

Y denotes carboxyl, carbalkoxy, carbophenoxy, cyano, carbamid or carbochloride, $R^7$ and $R^8$ are identical or different and denote hydrogen, lower alkyl or phenyl, or together can form a ring, by means of an ethylene or propylene bridge, and A' denotes a straight-chain or branched, saturated or unsaturated bivalent hydrocarbon radical with 1 to 15 carbon atoms, which can be substituted by phenyl which itself is optionally substituted by lower alkyl or halogen or by Y or the group

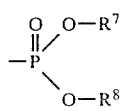

wherein

Y, $R^7$ and $R^8$ have the abovementioned meaning, in the presence of an acid.

The process according to the invention can be illustrated, for example, with the aid of the following equation:

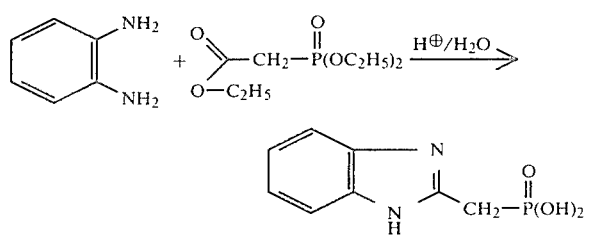

Carbalkoxy groups for the process according to the invention are carboxylic acid ester groups, the aliphatic part of which consists of a straight-chain or branched hydrocarbon radical, preferably of a lower alkyl radical with 1 to 6, in particular 1 to 2, carbon atoms.

Preferred o-arylenediamines for the process according to the invention are compounds of the formula

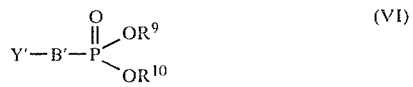

wherein $R^4$, $R^5$ and $R^6$ have the meaning indicated above.

The o-arylenediamines are known per se and can be prepared, for example, by reacting o-nitrochlorobenzenes with ammonia or primary amines and subsequently reducing the product.

The following o-arylenediamines may be mentioned as examples: o-phenylenediamine, 2,3- and 3,4-diaminotoluene, -ethylbenzene, -propylbenzene, -cumene, -isopropenylbenzene, -butylbenzene, -isobutylbenzene, -tert.-butylbenzene, -octylbenzene, -dodecylbenzene, -cyclohexylbenzene, -cyclohexenylbenzene, -diphenyl, -chlorobenzene, -bromobenzene, -trifluoromethylbenzene, -fluorobenzene, -nitrobenzene, -methoxybenzene and -butoxybenzene, 1,2-diamino-3,4-xylene, 1,2-diamino-3,5-xylene, 1,2-diamino-3-ethyl-6-methylbenzene, 1,2-diamino-3,4,6-trimethylbenzene, 2,3-diamino-5-chlorotoluene, 1,2-diamino-3,5-dichlorobenzene, 1,2-diamino,3,4,5-trichlorobenzene, 3,4-diamino-6-nitrotoluene, 3,4-diamino-5-chloroanisole, 2,3-diamino-5-trifluoromethylchlorobenzene and 1,2- and 2,3-diaminonaphthalene, and, where appropriate, (isomer) mixtures thereof.

Preferred phosphonocarboxylic acid derivatives for the process according to the invention are compounds of the formula $$Y'-B'-\overset{\overset{O}{\|}}{P}\overset{OR^9}{\underset{OR^{10}}{}}$$ (VI)

wherein

Y' denotes carboxyl, carbalkoxy or cyano,

B' denotes methylene, ethylene, propylene, butylene, vinylene, phenylvinylene, carboxy-, carbalkoxy- or cyano-ethylene or -propylene, dicarboxy-, dicarbalkoxy- or dicyano-propylene or -butylene or carboxy-, carbalkoxy- or cyano-phosphonobutylene or -dialkoxy-phosphonobutylene and $R^9$ and $R^{10}$ are identical or different and represent hydrogen or lower alkyl, in particular methyl or ethyl.

Phosphonocarboxylic acid derivatives for the process according to the invention are known per se; G. M. Kosolapoff, Organophosphorus Compounds, New York, John Wiley and Sons, Inc., (1950), 121 et seq.; G. M. Kosolapoff and L. Maier, Organic Phosphorus Compounds, volume 7, chapter 18, "Phosphonic Acids and Derivates", John Wiley and Sons, New York (1976); Houben-Weyl, Methoden der Organischen Chemie (Methods of Organic Chemistry), volume XII/1, Organische Phosphorverbindungen (Organic Phosphorus Compounds), page 348 et seq.; and German Offenlegungsschrift No. 2,015,068; German Offenlegungsschrift No. 2,333,151; German Offenlegungsschrift No. 2,333,353; German Offenlegungsschrift No. 2,602,030; Japanese Patent Specification No. 77,807 (9.7.1974); German Offenlegungsschrift No. 2,621,604 and German Offenlegungsschrift No. 2,621,605, and they can be prepared, for example, by reacting halogenoalkylcarboxylic acid compounds with trialkylphosphites or by adding dialkylphosphites onto $(\alpha,\beta)$-unsaturated carboxylic acid derivatives.

The following phosphonocarboxylic acid compounds may be mentioned as examples: phosphono -acetic acid, -propionic acid, -butyric acid, -isobutyric acid, -pivalic acid, -valeric acid, -isovaleric acid, -caproic acid, -isocaproic acid, -enanthic acid, -caprylic acid, -capric acid, -lauric acid, -stearic acid, -acrylic acid, -methacrylic acid, -crotonic acid, -allylacetic acid, -hexenoic acid, -undecenoic acid, -cinnamic acid, -chlorocinnamic acid, -methylcinnamic acid, -methoxycinnamic acid, -cyclobutanecarboxylic acid, -cyclopentanecarboxylic acid, -cyclohexanecarboxylic acid, -cyclohexenecarboxylic acid, -cyclohexylacetic acid, -cyclohexylcaproic acid, -phenylacetic acid, -chlorophenyl- acetic acid, -bromophenylacetic acid, -dihydrocinnamic acid, -methyldihydrocinnamic acid, -phenylpropionic acid, -chlorophenylbutyric acid, -phenylacrylic acid, -malonic acid, -methylmalonic acid, -cyclohexylmalonic acid, -maleic acid, -fumaric acid, -succinic acid, -ethylsuccinic acid, -dimethylsuccinic acid, -allylsuccinic acid, -butylsuccinic acid, -benzylsuccinic acid, -phenylsuccinic acid, -glutaric acid, -methylglutaric acid, -dimethylglutaric acid, -methylphenylglutaric acid, -adipic acid, -trimethyladipic acid, -pimelic acid, -ethanetricarboxylic acid, -propanetricarboxylic acid, -butanetricarboxylic acid, -pentanetricarboxylic acid, -hexanetricarboxylic acid and heptanetricarboxylic acid; diphosphono -butyric acid, -valeric acid, -isovaleric acid, -caproic acid, -isocaproic acid, -pimelic acid, -butanedicarboxylic acid and -pentanedicarboxylic acid; and triphosphono-pentanecarboxylic acid and the nitriles, amides, chlorides or esters, if appropriate mixed, such as methyl, ethyl, propyl, butyl and phenyl esters of the phosphono-, diphosphono- and triphosphono-carboxylic acids.

The process according to the invention can also be carried out without also using additional acids, especially if the starting compounds of the formula (IV) themselves contain phosphonic acid radicals. As a rule, however, acids are employed for the process according to the invention. Acids which may be mentioned are any proton acids, especially strong proton acids, with the exception of those which can react with the starting substances of the formula (III) to give benzimidazoles, for example carboxylic acids.

Examples which may be mentioned are mineral acids, such as hydrochloric acid, hydrobromic acid, sulphuric acid, phosphoric acid and/or nitric acid, and organic acids, such as phosphonic acids and sulphonic acids, such as methanesulphonic acid, benzenesulphonic acid and toluenesulphonic acid. The acids can be employed individually or as mixtures, and preferably in aqueous solution.

The concentration of the acids in the reaction mixture can be varied within wide limits and depends on their nature, properties and solubility. The acid is in general used in the reaction solution in a concentration of 5 to 80% by weight, preferably in a concentration of 10 to 50% by weight.

The process according to the invention can in general be carried out in a temperature range from 50° to 200° C., preferably from 80° to 120° C. It is generally carried out under normal pressure. However, one can carry out the process according to the invention under reduced or increased pressure.

The process according to the invention can be carried out either discontinuously or continuously.

In general, the starting compounds are reacted with one another in an approximately stoichiometric ratio; however, it can also be advantageous to employ the o-arylenediamine or the phosphonocarboxylic acid in an excess of, for example, 5 to 50%, preferably 10 to 25%.

The amount of aqueous acid in the reaction medium can vary within wide limits and depends largely on the nature of the acid, the solubility of the starting materials and end products and the reactivity of the starting substances. In general, 0.5 to 5 parts by weight of acid, preferably 1 to 3 parts by weight of acid, relative to the o-arylenediamine, are employed in the process according to the invention. The starting substances are generally mixed with the aqueous acid at room temperature and the mixture is warmed to the reaction temperature under an inert gas, for example nitrogen or a noble gas. However, it is also possible to add one of the two starting compounds to a solution or suspension of the other at the reaction temperature, or to introduce both the starting compounds into the reaction medium at the reaction temperature.

The benzimidazolyl-2-alkane-phosphonic acids prepared by the process according to the invention are worked up, isolated and purified in the customary manner, for example by neutralizing the reaction mixture until the isoelectric point of the benzimidazolylphosphonic acids is reached and filtering off the product and recrystallizing or reprecipitating it.

It has furthermore been found that the benzimidazolyl-2-alkane-phosphonic acids and their salts have a pronounced corrosion-inhibiting effect and can be used as corrosion inhibitors. For the inhibition of corrosion, they can be employed individually, as combinations with one another or together with other known corrosion inhibitors, such as, for example, sodium benzoate, sodium cinnamate, sodium nitrite, sodium nitrate, borax, alkali metal phosphates, molybdates, chromates or silicates, alkanolamines or zinc compounds. For the inhibition of corrosion, the compounds according to the invention are in general added to aqueous, aqueous-alcoholic, alcoholic and/or oil-containing media; For example, they can be employed as corrosion inhibitors in the heat transfer media of cooling cycles or heating cycles, cooling lubricants, motor oils or as pickling inhibitors. Corrosion of metals, especially of copper and alloys thereof, steel, cast iron, solder, aluminum and aluminum alloys, is prevented by adding the substances of the formula (I) according to the invention and/or their salts to the media or circulating fluids mentioned.

The concentration of inhibitor to be used depends on the system to be inhibited. In general, the corrosion inhibitors according to the invention are employed in concentrations of 0.0001 to 0.3% by weight, preferably of 0.001 to 0.05% by weight, relative to the total amount of medium to be inhibited.

Compared with known corrosion inhibitors, such as organic mercapto compounds or triazole derivatives, the benzimidazolyl-2-alkane-phosphonic acids according to the invention have, for example, the following advantages: stability and effectiveness over a wide pH range; stability towards oxidation, especially towards oxidation by atmospheric oxygen; good stability to heat; resistance to hydrolysis; and good solubility, especially in aqueous basic media which are used, for example, as circulating fluids in combustion engines.

The new benzimidazolylalkanephosphonic acids and their alkali metal salts are very suitable as wetting agents in the preparation of highly concentrated aqueous suspensions of pigments and fillers substances which are practically insoluble in the medium used. Fillers are for example kaolin, karite, chalk, dolimite and aluminium silicates. Highly concentrated in this context is generally understood as a solids content of above about 45% by weight, relative to the weight of the supension, depending on the pigment employed. Such suspensions of pigments and fillers are frequently called slurries (German Offenlegungsschfriften Nos. 2,237,791, 2,233,517, 1,135,535, 2,045,141, 1,810,041, 2,044,510 and 2,611,768).

The advantages in processing these slurries compared with the pulverulent pigment and filler are described in detail in the above-mentioned offenlegungsschrifts.

Metering of the compounds to be used according to the invention to the pigments and fillers presents no difficulties, since they are soluble in dilute alkalis (NaOH, KOH, NH4OH etc.). They can therefore either be added to the water in which the pigment is to be dispersed or can already be applied to the surface of the pigment during the preparation process, for example before or during the final grinding in a peg mill, ball mill, vibratory mill or jet mill.

In a particularly preferred embodiment, filter cakes which have a relatively high solids content (25 to 60%) and are difficult to convey can be "liquefied" by adding the compounds according to the invention and in this form can easily be conveyed (for example by pumping), for example to a subsequent drying unit or calcining unit.

The point in the production of the pigment or filler at which the compounds used according to the invention are added is not of decisive importance.

The amount of substances according to the invention added is 0.02 to 2, preferably 0.1 to 1, % by weight, relative to the solids, depending on the pigment or filler.

EXAMPLE 1

534 g (2.22 mols) of triethyl 3-phosphonopropionate are allowed to run into a boiling solution of 259 g (2.4 mols) of o-phenylenediamine in 1,000 g of H₂O and 1,000 g of concentrated hydrochloric acid in the course of 30 minutes, whilst passing nitrogen over the mixture and whilst stirring, and the mixture is kept at the reflux temperature for a further 15 to 20 hours. After cooling the mixture, the solid is redissolved by carefully adding (cooling!) 1,200 g of 45% strength sodium hydroxide solution and about 500 to 1,000 ml of H₂O and the brown solution is extracted by shaking several times with methylene chloride, until the methylene chloride phase remains colourless. The aqueous phase is then heated to the reflux temperature for 30 minutes, using a large amount of active charcoal, and, after filtration, the filtrate is adjusted to pH 4.5 with hydrochloric acid. Light-coloured to brownish crystals are obtained. The crystals are filtered off, suspended several times in warm water, filtered off and washed with water until free from chloride. On concentrating the mother liquors and wash waters in vacuo, further material is obtained, which is purified in the same manner. After drying the product in vacuo over P₂O₅, 405 g (80.4% of theory) of 2-[benzimidazol-2-yl]-ethanephosphonic acid are obtained as a light beige to colourless powder which does not melt up to a temperature of 300° C.

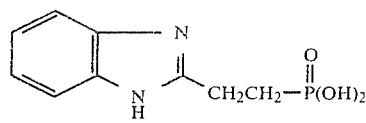

calculated: C 47.8, H 4.90, N 12.39, P 13.70.
Found: C 47.5, H 4.88, N 12.60, P 14.05.

EXAMPLE 2

905 g (4.0 mols) of triethyl phosphonoacetate are allowed to run into a boiling solution of 472 g (4.2 mols) of O-phenylenediamine in 3,200 g of half-concentrated hydrochloric acid in the course of 30 minutes, whilst passing nitrogen over the mixture and whilst stirring, and the mixture is kept at the reflux temperature for a further 18 hours. After cooling the mixture, it is carefully rendered alkaline with 3,200 g of 25% strength sodium hydroxide solution, the solution is extracted by shaking 3 times with about 700 ml of CH₂Cl₂ each time, the aqueous phase is then boiled up with active charcoal for 30 minutes and, after filtering the mixture, the light clear solution is adjusted to pH 5 with concentrated HCl. The crystals which have precipitated are filtered off and washed free from Cl by being suspended several times in lukewarm water. After drying the product over P₂O₅ in a drying cabinet, 553 g (65% of theory) of benzimidazol-2-yl-methanephosphonic acid are obtained as a light beige to colourless powder which does not melt up to a temperature of 300° C.

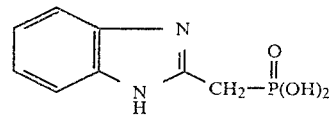

Calculated: C 45.29, H 4.28, N 13.21, P 14.60.
Found: C 45.55, H 4.32, N 13.55, P 14.95.

EXAMPLE 3

A mixture of 200 g of H₂O, 200 g of concentrated H₂SO₄, 60 g (0.55 mol) of o-phenylenediamine and 113.1 g (0.5 mol) of triethyl phosphonoacetate is kept at the reflux temperature for 25 hours, whilst passing nitrogen over, and, after cooling, the solution is rendered alkaline by adding 500 g of 40% strength sodium hydroxide solution and diluting with about 1,500 ml of water and is further worked up as described in Example 2. 76 g (71.5%) of benzimidazol-2-yl-methanephosphonic acid are obtained.

EXAMPLE 4

165 g of H₂O, 235 g of 85% strength H₃PO₄, 60 g (0.55 mol) of o-phenylenediamine and 113.1 g (0.5 mol) of triethyl phosphonoacetate are mixed and the mixture is heated to the reflux temperature for 48 hours, whilst passing nitrogen over. When, after cooling, the dark solution is rendered alkaline with about 250 g of concentrated ammonia, and 1,000 ml of H₂O, and is worked up analogously to Example 2, 71 g (66.8% of theory) of benzimidazol-2-yl-methanephosphonic acid are obtained.

EXAMPLE 5

95.6 g (0.5 mol) of phosphonopropionitrile diethyl ester, 60 g (0.55 mol) of o-phenylenediamine, 350 g of concentrated HCl and 200 g of H₂O are heated to the reflux temperature for 16 hours, whilst passing nitrogen over the mixture. Active charcoal is then added to the dark solution and the mixture is kept at the reflux temperature for a further 30 minutes and filtered and the light-reddish solution is adjusted to pH 3 with about 250 g of 45% strength sodium hydroxide solution. The grey to colourless crystals of 2-[benzimidazol-2-yl]-ethanephosphonic acid are filtered off and washed free from Cl⁻ by being suspended in water and filtered off several times. After drying, 92.2 g (85% of theory) of product are obtained.

| Ex. | Starting substance | X | R | Melting point | Yield (%) |
|---|---|---|---|---|---|
| 7 | 3,4-Diaminotoluene | 5-CH₃ | H | — | 55.7 |
| 8 | 4-Chloro-1,2-diaminobenzene | 5-Cl | H | — | 71.3 |
| 9 | o-Toluylenediamine+ (approximately 1:1 isomer mixture) | 4(5)-CH₃ | H | — | 53.5 |
| 10 | N-Benzyl-o-phenylene diamine | H | CH₂C₆H₅ | — | 61.7 |
| 11 | N-Phenyl-o-phenylene diamine | H | C₆H₅ | — | 32 |

The following compounds were prepared analogously to Example 1, using trimethyl 3-phosphonopropionate instead of triethyl 3-phosphonopropionate:

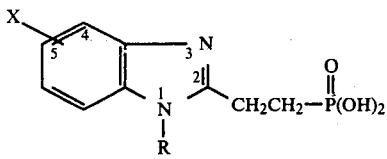

+2,3- and 3,4-diaminotoluene

| Example | Starting substance | X | R | Melting point | Yield (%) |
|---|---|---|---|---|---|
| 12 | N-Methyl-o-phenylenediamine | H | CH₃ | 228° C.++ | 62 |
| 13 | 4-Nitro-1,2-diaminobenzene | 5-NO₂ | H | — | 33.5 |
| 14 | 4-Methoxy-1,2-diaminobenzene | 5-OCH₃ | H | — | 59 |
| 15 | o-Toluylenediamine+ (approximately 1:1 isomer mixture) | 4(5)-CH₃ | H | 280° C., decomposition | 82.7 |

EXAMPLE 6

226.2 g (1 mol) of triethyl phosphonoacetate, 220 g (1.05 mols) of 4,5-diamino-1,3-dimethylbenzene dihydrochloride (97% pure), 400 g of H₂O and 300 g of concentrated HCl are reacted with one another analogously to Example 2. 195 g (81% of theory) of 4,6-dimethylbenzimidazol-2-yl-methanephosphonic acid are obtained as light-brownish crystals which do not melt below 300° C.

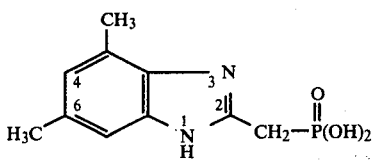

Calculated: C 50.0, H 5.46, N 11.66, P 12.89.
Found: C 50.0, H 5.81, N 11.5, P 12.7.

The following compounds were prepared analogously to Example 2:

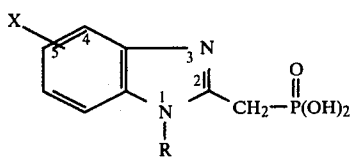

EXAMPLE 16

If 110 g (0.43 mol) of triethyl 4-phosphonobutyrate and 48.6 g (0.45 mol) of o-phenylenediamine are reacted with one another in 200 g of concentrated HCl and 200 g of H₂O according to Example 1, 52.5 g (51.5% of theory) of 3-[benzimidazol-2-yl]-propanephosphonic acid are obtained as light grey crystals with a melting point of about 280° C. (decomposition).

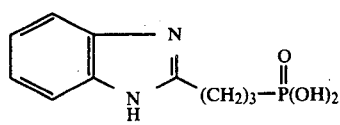

Calculated: C 50.00, H 5.46, N 11.66, P 12.89. Found: C 50.30, H 5.17, N 11.75, P 13.20.

EXAMPLE 17

86.5 g (0.80 mol) of o-phenylenediamine are reacted with 167 g (0.75 mol) of methyl diethylphosphonoacrylate in 600 g of half-concentrated hydrochloric acid according to Example 1. The yield of 2-[benzimidazol-2-yl]-vinylphosphonic acid as beige to colourless crystals which do not melt is 75.8% of theory (128 g).

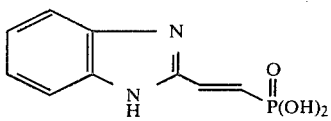

Calculated: C 48.22, H 4.05, N 12.50, P 13.82. Found: C 48.30, H 4.35, N 12.45, P 14.12.

The following compounds are obtained according to the procedure of Example 1, using ethyl 3-dimethylphosphonobutyrate:

| Example | Starting substances | X | Melting point | Yield (%) |
|---|---|---|---|---|
| 18 | 2,3-Diaminotoluene | 4-$CH_3$ | — | 69.7 |
| 19 | o-Toluylenediamine (approximately 1:1 isomer mixture) | 4(5)-$CH_3$ | — | 61.3 |

The following compounds are obtained according to the procedure of Example 1, using diethyl dimethylphosphonosuccinate:

| Example | Starting substances | X | Melting point | Yield (%) |
|---|---|---|---|---|
| 20 | o-Phenylenediamine | H | — | 73.4 |
| 21 | 3,4-Diaminotoluene | 5-$CH_3$ | — | 61.7 |

EXAMPLE 22

If 78 g (0.25 mol) of triethyl 2-phosphonocinnamate are reacted with 32.5 g (0.3 mol) of o-phenylenediamine in 300 g of half-concentrated hydrochloric acid analogously to Example 1, 25 g (33.3% of theory) of β-[benzimidazol-2-yl]-β-styrenephosphonic acid are obtained as beige crystals which do not melt.

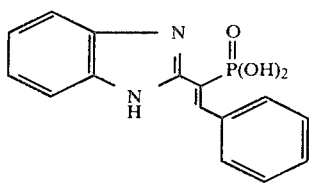

Calculated: C 60.00, H 4.36, N 9.33, P 10.32. Found: C 58.99, H 4.59, N 9.59, P 10.80.

EXAMPLE 23

40.5 g (0.375 mol) of o-phenylenediamine, 271.2 g (0.5 mol) of phosphonobutanetricarboxylic acid (50% strength in water) and 100 ml of water are heated at the reflux temperature under nitrogen for 30 hours. After cooling the mixture, the crystals which have separated out are filtered off and recrystallized from 15 parts of water, active charcoal being added. 63.5 g (49.6% of theory) of 3-[benzimidazol-2-yl]-1-carboxy-1-carboxymethyl-propanephosphonic acid are obtained as colourless crystals which do not melt.

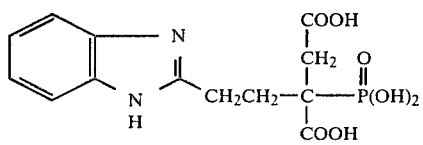

Calculated: C 45.45, H 4.38, N 8.20, P 9.05. Found: C 45.10, H 4.13, N 8.37, P 9.35.

EXAMPLE 24

Test as a corrosion inhibitor

65×23×2 mm pickled and degreased copper sheets were used as test pieces; the test solution used was synthetic seawater according to ASTM D 665-IP 135, to which the particular corrosion inhibitor to be tested was added. Throughout the experimental period of 7.5 hours, the test pieces were immersed completely in the test solution, which was warmed to 55° C. and into which about 100 ml of air were passed per minute.

After this test, the test pieces were cleaned for 15 seconds in half-concentrated hydrochloric acid and washed with water and acetone. The dry test pieces were weighed before and after the experiment. The losses in weight thus obtained per m² of surface and the appearance of the test pieces and the test solution after the experiments are shown in Table I.

TABLE I

| Corrosion inhibitor | Concentration used, in ppm | Loss in weight per unit area in g/m² | Appearance, after the test, of the test pieces | of the test solution |
|---|---|---|---|---|
| None | — | 3.25 | highly corroded | severe precipitation of copper salts |
| 1-Carboxy-2-[5-methylbenzimidazol-2-yl]-ethanephosphonic acid (Example 21) | 50 | 0.66 | slight dark tarnish colour | clear |
| 2-[5-Nitrobenzimidazol-2-yl]-ethanephosphonic acid (Example 13) | 50 | 0.36 | slight dark tarnish colour | clear |
| 2-[Benzimidazol-2-yl]-1-carboxy-ethanephosphonic acid (Example 20) | 50 | 0.93 | slight dark tarnish colour | trace of precipitation of copper salts |
| 2-[4(5)-Methylbenzimidazol-2-yl]-ethane- | 50 | 0.69 | slight dark | trace of precipi- |

TABLE I-continued

| Corrosion inhibitor | Concentration used, in ppm | Loss in weight per unit area in g/m$^2$ | Appearance, of the test pieces | after the test, of the test solution |
| --- | --- | --- | --- | --- |
| phosphonic acid (Example 15) | | | tarnish colour | tation of copper salts |
| [5-Chlorobenzimidazol-2-yl]-methane-phosphonic acid (Example 8) | 50 | 0.27 | slight dark tarnish colour | clear |
| 3-[Benzimidazol-2-yl]-propanephosphonic acid (Example 16) | 50 | 0.72 | slight dark tarnish colour | trace of precipitation of copper salts |

EXAMPLE 25

Preparation of a highly concentrated aqueous suspension of titanium dioxide which is pourable and stable on storage, with the aid of benzimidazolylalkanephosphonic acids A commercial product, that is to say an untreated anatase with a TiO$_2$ content of 99%, was used as the pigment. Because of the Raymond grinding which has been carried out, the pigment is readily dispersible.

The amounts of auxiliaries and wetting agents used in the preparation of the slurry were 0.3% of the substances according to the invention, relative to the TiO$_2$ pigment.

As a comparison test, one slurry was prepared without any addition of a wetting agent and another slurry was prepared with 0.3% of polyphosphate (A), which is an auxiliary widely used for this field of application.

The slurries were prepared by first initially introducing the auxiliary or wetting agent (for example 2.16 g) in the form of a 10% strength alkaline solution. In order to avoid any influence of the high degree of hardness of the tap water available, the tests were carried out only with distilled water. Water is then added according to the solids content desired later (for example 28.00 g minus 2.16 g=25.84 g). The amount of pigment weighed out (for example 72 g) is then added, whilst stirring. Thereafter, the entire suspension is dispersed for about 15 minutes with the aid of a dissolver, at as high as possible a speed of rotation.

The viscosities measured should then be as low as possible at a solids content which is as high as possible. The viscosities [Pascal.seconds, abbreviated to Pa.sec] are determined with the aid of a rotating viscometer, if possible at the same rate of shearing $D[s^{-1}]$ or at the highest possible rate of shearing in each case. The measurements are made after 1 day and after storage for about 2 to 3 weeks.

For a good slurry it is important that not only does the viscosity remain constant as far as possible but that as little sediment as possible is formed during the storage time of about 2 to 3 weeks, or that a sediment can easily be stirred up again. This test was carried out by stirring the slurries manually, using a spatula. Significant differences in the storage stability properties can be established rapidly and well using this relatively coarse method.

The results can be seen in Table II.

In comparison to the blank sample, without a wetting agent, it is found that the substances according to the invention are particularly suitable as a result of having a higher solids content and at the same time a lower viscosity. With regard to the comparison wetting agent, the stability on storage (viscosity, sediment and processability) of the slurries prepared with the substances according to the invention is significantly better.

EXAMPLE 26

Preparation of a highly concentrated aqueous suspension of TiO$_2$ which is pourable and stable on storage The preparation and measurement of the slurries were carried out as described under Example 25.

A commercial product, that is to say an untreated anatase pigment with a TiO$_2$ content of 99%, was again used as the pigment. In contrast to the anatase pigment used in Example 25, this pigment is distinguished by a particularly good dispersibility as a result of having been ground in a jet mill.

The results can be seen in Table III. In comparison to the blank sample, the slurries with the wetting agents have a higher solids content. The suspensions containing the substances according to the invention have more favourable storage stability properties than the suspension containing polyphosphate (A).

EXAMPLE 27

Preparation of a highly concentrated aqueous suspension of iron oxide yellow which is pourable and stable on storage A commercial product, that is to say an iron oxide yellow pigment ($\alpha$FeOOH) with a Fe$_2$O$_3$ content of 86% and a predominant particle size of the needle-shaped primary particles of 0.1×0.7 $\mu$m, was used as the pigment.

In addition to the blank sample, slurries containing polyphosphate (A) and aminotrimethylenephosphonic acid (B) were prepared as comparison slurries.

The preparation and measurement of the slurries were carried out as described under Example 25.

The results can be seen in Table IV.

In the case of this pigment which is difficult "to liquefy" (as a result of the needle-like structure of the primary particles), the differences between the blank sample and the slurries containing wetting agents are less than in the case of Examples 25 and 26. The storage properties of the substances according to the invention are more favourable than those of comparison substances A and B.

EXAMPLE 28

Preparation of a highly concentrated aqueous suspension of iron oxide black which is pourable and stable on storage A commercial product, that is to say an iron oxide black pigment (Fe$_3$O$_4$) containing 94% of Fe$_2$O$_3$, was used as the pigment. In addition to the blank sample, suspensions containing polyphosphate (A) and 2-aminophosphonobutane-1,2,4-tricarboxylic acid (C) were used as comparison slurries.

The preparation and testing of the slurries were carried out according to Example 25.

The results are summarised in Table V.

Slurries with a solids content of 65% can be prepared using the substances according to the invention and the comparison wetting agents (the blank sample has a solids content of only 60%). All the slurries have a good stability on storage. The properties of the wetting agents used for comparison and the substances according to the invention are equally good.

EXAMPLE 29

Preparation of a highly concentrated aqueous suspension of $TiO_2$ which is pourable and stable on storage The preparation and testing of the slurries were carried out as indicated under Example 25.

The results can be seen in Table VI.

In addition to the blank sample, the abovementioned wetting agents A, B and C were again used in the comparison slurries.

Compared with the blank sample, the substances according to the invention and the other wetting agents give slurries with significantly higher solids contents.

TABLE II

| Wetting agent | % | S | Viscosity after 1 day $D[s^{-1}]$ Pa.sec | | after 10 days $D[s^{-1}]$ Pa.sec | | General appearance after 10 days |
|---|---|---|---|---|---|---|---|
| — | — | 65 | 98.3 | 13.1 | 98.3 | 13.2 | pasty, still workable |
| A | 0.3 | 72 | 79.37 | 19.5 | | nm | solid, no longer workable |
| Example 20 | 0.3 | 72 | 137.1 | 1.9 | 59.2 | 4.3 | possesses slight structural viscosity, immediately liquid after light stirring, readily workable |
| Example 21 | 0.3 | 72 | 137.1 | 1.3 | 137.1 | 1.9 | light stirring, readily workable |

S = solids [%]
nm = not measurable as a result of too high a viscosity or of a solid sediment which can no longer be stirred up

TABLE III

| Wetting agent | % | S | Viscosity after 1 day $D[s^{-1}]$ Pa.sec | | after 14 days $D[s^{-1}]$ Pa.sec | | General appearance after 14 days |
|---|---|---|---|---|---|---|---|
| — | — | 65 | 43.35 | 0.09 | 43.35 | 0.09 | possesses structural viscosity; readily workable |
| A | 0.3 | 72 | | nm | | nm | solid; no longer workable |
| Example 8 | 0.3 | 72 | 42.45 | 12.1 | 42.45 | 12.7 | pasty, still workable |
| Example 9 | 0.3 | 72 | 42.45 | 15.8 | 42.45 | 16.7 | pasty, still workable |

TABLE IV

| Wetting agent | % | S | Viscosity after 1 day $D[s^{-1}]$ Pa.sec | | after 14 days $D[s^{-1}]$ Pa.sec | | General appearance after 14 days |
|---|---|---|---|---|---|---|---|
| — | — | 48 | 98.3 | 6.4 | 98.3 | 5.6 | pasty, workable |
| A | 0.3 | 50 | | nm | | nm | |
| B | 0.3 | 50 | 111.2 | 0.02 | | nm | |
| Example 21 | 0.3 | 50 | 103.9 | 1.4 | 98.3 | 3.2 | pasty, workable |
| Example 9 | 0.3 | 50 | 98.3 | 4.4 | 98.3 | 4.4 | pasty, workable |
| Example 15 | 0.3 | 50 | 98.3 | 6.2 | 98.3 | 4.3 | pasty, workable |
| Example 8 | 0.3 | 50 | 103.9 | 1.1 | 103.9 | 1.3 | slightly pasty, workable |

TABLE V

| Wetting agent | % | S | Viscosity after 1 day $D[S^{-1}]$ Pa.sec | | after 14 days $D[s^{-1}]$ Pa.sec | | General appearance after 14 days |
|---|---|---|---|---|---|---|---|
| — | — | 60 | 103.9 | 1.1 | 98.3 | 1.4 | slightly pasty, workable |
| A | 0.3 | 65 | 98.3 | 2.5 | 98.3 | 2.7 | slightly pasty, workable |
| C | 0.3 | 65 | 103.9 | 1.6 | 98.3 | 2.0 | slightly pasty, workable |
| Example 9 | 0.3 | 65 | 98.3 | 2.4 | 98.3 | 2.6 | slightly pasty, workable |
| Example 21 | 0.3 | 65 | 103.9 | 1.7 | 98.3 | 1.7 | slightly pasty, workable |

TABLE VI

| Wetting agent | % | S | Viscosity after 1 day $D[s^{-1}]$ Pa.sec | | after 14 days $D[^{-1}]$ Pa.sec | | General appearance after 14 days |
|---|---|---|---|---|---|---|---|
| — | — | 63 | 103.9 | 2.1 | 98.3 | 3.0 | slightly pasty, workable |
| A | 0.3 | 72 | 111.2 | 0.09 | 111.2 | 0.14 | possesses structural viscosity; immediately liquid after stirring |
| B | 0.3 | 72 | 111.2 | 0.05 | 111.2 | 0.08 | readily workable |
| C | 0.3 | 72 | 111.2 | 0.03 | 111.2 | 0.03 | liquid, readily workable |
| Example 8 | 0.3 | 72 | 103.9 | 0.31 | 103.9 | 0.93 | viscous, workable |
| Example 7 | 0.3 | 72 | 103.9 | 0.83 | 103.9 | 1.42 | viscous, workable |

TABLE VI-continued

| | | | Viscosity | | | |
|---|---|---|---|---|---|---|
| Wetting agent | % | S | after 1 day $D[s^{-1}]$Pa.sec | | after 14 days $D[^{-1}]$Pa.sec | General appearance after 14 days |
| Example 17 | 0.3 | 72 | 103.9 | 0.82 | 103.9 1.17 | viscous, workable |

ADDITIONAL EXAMPLE

The procedure is analogous to Example 23, 306 g (0.5 mol) of 2-phosphono-2-(2-phosphonoethyl)-succinic acid (50% strength in water), 54 g (0.5 mol) of o-phenylenediamine and 100 ml of water being heated to the reflux temperature under nitrogen for 7 hours. The grey crystals are filtered off, taken up in 1,000 ml of water and dissolved with a little dilute NaOH and the solution is boiled up with active charcoal and filtered. After acidifying the filtrate to pH 2 with dilute $H_2SO_4$, lightreddish crystals precipitate and are filtered off and washed with water. On concentrating the mother liquors and wash waters, further crystals are obtained. After drying, the yield of 4-benzimidazol-2-yl-3-carboxy-butane-1,3-diphosphonic acid is 141 g (74.5% of theory).

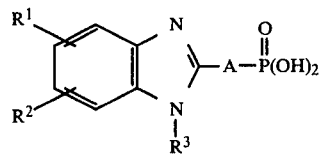

Calculated: C 38.11, H 4.26, N 7.41, P 16.38. Found: C 37.7, H 5.05, N 7.34, P 16.45.

What is claimed is:

1. A benzimidazolyl-2-alkane-phosphonic acid of the formula

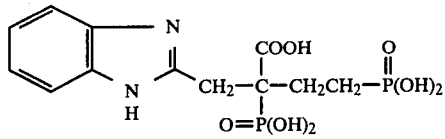

wherein
$R^1$ and $R^2$ are identical or different and denote hydrogen, lower alkyl, phenyl, halogen, trifluoromethyl, nitro or lower alkoxy, or together form a fused-on benzene ring,
$R^3$ denotes hydrogen, lower alkyl or phenyl or benzyl which is optionally substituted by lower alkyl or halogen and
A denotes a straight-chain or branched, saturated or unsaturated bivalent hydrocarbon radical with 1 to 15 carbon atoms, which can be substituted by phenyl which is optionally substituted by lower alkyl or halogen or by carboxyl or the phosphonic acid group,
and its salt with an inorganic base or acid.

2. A benzimidazolyl-2-alkane-phosphonic acid according to claim 1 of the formula

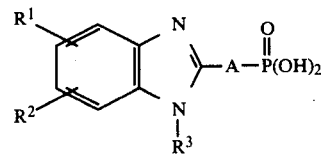

wherein
$R^4$ and $R^5$ are identical or different and denote hydrogen, methyl, chlorine, methoxy or nitro,
$R^6$ denotes hydrogen, methyl, benzyl or phenyl and
B denotes methylene, ethylene, propylene, butylene, vinylene, phenylvinylene, carboxyethylene, carboxypropylene, dicarboxypropylene, dicarboxybutylene, phosphonopropylene, phosphonobutylene or carboxydiphosphonobutylene.

3. A benzimidazolyl-2-alkane-phosphonic acid according to claim 1 wherein A is a straight chain or branched saturated or unsaturated bivalent hydrocarbon radical of 1 to 12 carbon atoms.

4. A benzimidazolyl-2-alkane-phosphonic acid according to claim 1 wherein A is a straight chain or branched saturated or unsaturated bivalent hydrocarbon radical with 1 to 6 carbon atoms.

5. A benzimidazolyl-2-alkane-phosphonic acid according to claim 1 wherein A is selected from the group consisting of methylene, ethylene, vinylene, propylene, butylene, butenylene, pentylene, hexylene, hexenylene, heptylene, octylene, decylene and dodecylene which radicals can be substituted by phenyl, tolyl, ethylphenyl, xylyl, chlorophenyl, carboxyl and/or phosphono.

6. A benzimidazolyl-2-alkane-phosphonic acid of the formula

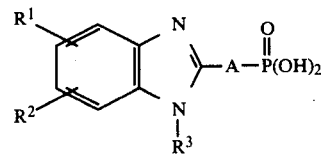

wherein
$R^1$ and $R^2$ are identical or different and denote hydrogen, lower alkyl, phenyl, halogen, trifluoromethyl, nitro or lower alkoxy, or together form a fused-on benzene ring,
$R^3$ denotes hydrogen, lower alkyl or phenyl or benzyl which is optionally substituted by lower alkyl or halogen and
A denotes cyclohexylene and cyclopentylene, and its salt with an inorganic base or acid.

* * * * *